United States Patent [19]

Ho et al.

[11] 4,240,969

[45] Dec. 23, 1980

[54] SYNTHESIS OF MENTHOFURAN

[75] Inventors: T. L. Ho; Zia U. Din; Sean G. Traynor, all of Jacksonville, Fla.

[73] Assignee: SCM Corporation, New York, N.Y.

[21] Appl. No.: 72,182

[22] Filed: Sep. 4, 1979

[51] Int. Cl.³ .................. C07D 307/79; C07D 303/12
[52] U.S. Cl. .......................... 260/346.22; 260/348.12; 260/348.57
[58] Field of Search ....................... 260/346.22, 348.12

[56] References Cited

FOREIGN PATENT DOCUMENTS 54-73766  6/1979  Japan .

OTHER PUBLICATIONS

Frietel et al., J. Org. Chem., 23, p. 481 (1958).
Treibs, Ber. 70, 85 (1937).
Zalkow et al., J. Org. Chem. 28, 1705 (1963).
Fieser et al., Reagents for Organic Synthesis, Wiley Publ. Co., (1967), pp. 145-146.
Wenkert et al. J. Am. Chem. Soc. 99, p. 4778 (1977).
Stetter et al. Ber., 93, 603 (1960).

*Primary Examiner*—Henry R. Jiles
*Assistant Examiner*—Bernard Dentz
*Attorney, Agent, or Firm*—Merton H. Douthitt; Gordon P. Becker

[57] ABSTRACT

A new process for synthesizing menthofuran is disclosed. Said process comprises epoxidizing isopulegol to form the new compound isopulegol epoxide. The epoxide is then oxidized to form isopulegone epoxide which can be cyclodehydrated to form menthofuran.

13 Claims, No Drawings

SYNTHESIS OF MENTHOFURAN

BACKGROUND OF THE INVENTION

Menthofuran (3,6-dimethyl-4,5,6,7-tetrahydrocoumarone) naturally occurs in the oil obtained from flower buds of the peppermint plant and exercises a great effect on the aroma of that oil. Because this effect has not been duplicated by any other compound, menthofuran is important in the formulation of certain synthesized essential oils, such as peppermint oil. However, menthofuran is an expensive compound of limited availability.

In the past the methods used to synthesize menthofuran have either required expensive or relatively unavailable raw materials, or have suffered from poor yields. One advantage of the present process over those previously suggested is that it utilizes the relatively available inexpensive isopulegol as the starting material. Another advantage of the present process is that the reaction sequence is free of significant competing reactions. A further advantage of the present process is that menthofuran is produced in good yield.

SUMMARY OF THE INVENTION

The present invention is a new process for the synthesis of menthofuran. Said process utilizes isopulegol as the major reactant and follows a reaction sequence comprising epoxidation, oxidation, and cyclodehydration to form menthofuran, as shown in FIG. 1.

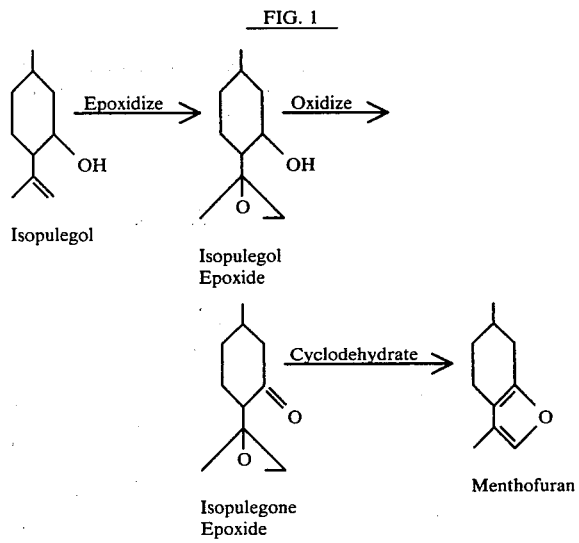

FIG. 1

In this disclosure, isopulegol (p-menth-8-en-3-ol) and isopulegone (p-menth-8-en-3-one) refer to all of the respective stereoisomers of these compounds and mixtures of the respective stereoisomers. The same is true for isopulegol epoxide (3-hydroxy-p-menthan-8,9-oxide) and isopulegone epoxide (p-menthan-3-one-8,9-oxide). These mixtures can be racemic or optically active and this property will carry through to the menthofuran formed.

DETAILED DESCRIPTION OF THE INVENTION

The starting material for the instant synthesis is isopulegol, which is readily available and can be obtained from the cyclization of citronellal. In the instant process isopulegol is first epoxidized to form isopulegol epoxide. The epoxidizing conditions for this step of the process can be conventional. Any useful general preparation for epoxides can be used as long as it is sufficiently mild so formation of undesirable byproducts does not take place. A suitable epoxidation is treatment with a peroxy-carboxylic acid (peracid) at about 0° C. and atmospheric pressure. Such conditions are preferred for efficiency and economy, but higher and lower temperatures (−20° to 50° C.) and pressures (0.1 to 10 atmospheres absolute) can be used in conventional fashion if necessary or desired.

Other conventional reagents for epoxidation which are useful include transition metal-hydroperoxide systems, nitrile-hydrogen peroxide systems and dehydrating agents-hydrogen peroxide systems. All of these are used in conventional fashion under conditions well known in the art and similar to the conditions stated above for epoxidation with a peracid.

The nitrile-hydrogen peroxide systems are preferred under some circumstances. This epoxidation procedure involves the use of an alkyl, aryl, or aralkyl nitrile containing 2 to 12 carbon atoms and hydrogen peroxide. This procedure is effective to obtain high yields even under very mild conditions, for example, pH 8. Thus, it can produce the desired epoxide with low levels of byproducts in an efficient manner.

The hydroxyl functionality of isopulegol epoxide is then oxidized to yield isopulegone epoxide. Any conditions effective for the oxidation of secondary alcohols can be used so long as they do not cause formation of undesired byproducts. The term "oxidizing conditions" as used herein, shall mean any set of conditions effective for the oxidation of secondary alcohols, broadly −100° to 150° C., and 0.1 to 10 atmospheres, and preferably −60° to 100° C. and 0.5 to 5 atmospheres using conventional oxidants such as chlorine/pyridine, chromate reagents, oxalyl chloride/dimethyl sulfoxide, Fetizon's reagent, the Moffatt oxidation system, and etc. These, and other sets of conditions which are included in the term "oxidizing conditions" are known to those skilled in the art and have been reviewed extensively as, for example, in Fieser and Fieser, *Reagents for Organic Synthesis*, Vol. 1–7, John Wiley & Sons, or in *Methoden Der Organischen Chemie* (Houben-Weyl), Band 4, Teil 16, Oxidation II, George Thieme Verlag, Stuttgart, 1975.

The chlorine/pyridine oxidation is well suited to this step of the instant process. This procedure involves reacting isopulegol epoxide in pyridine with chlorine at about room temperature (e.g. 20° C.) in a liquid state. Isopulegol epoxide can thus be oxidized to isopylegone epoxide in good yield. A particularly good yield can be obtained when there is only a slight molar excess of chlorine over isopulegol epoxide, and the yield has been found to decrease as the excess chlorine increases.

It was found, however, that treatment with aqueous hypochlorite and the Oppenauer oxidation both gave unsatisfactory results in our hands.

The isopulegone epoxide is then cyclodehydrated to form menthofuran. This cyclodehydration readily occurs in the presence of an acid or heat. Either a Lewis acid or a protic acid can be used provided it can create a sufficiently acidic environment. Hydrochloric acid is convenient because a tolerance to the chloride ion has already been demonstrated by the success of the chlorine/pyridine oxidation. Addition of a sufficient amount of a solution of about 9% HCl is effective for converting all of the isopulegone epoxide to menthofuran at room temperature and atmospheric pressure. However, lower concentrations are also effective, but the conversion is slower. Similarly, more concentrated acid solutions are also effective, but are considered wasteful, and extremes can be deleterious to the products. Isopulegone epoxide also can be cyclodehydrated to form menthofuran with heat. Raising the temperature of the isopulegone epoxide to 110° to 115° C. has been found effective to cause complete cyclodehydration to menthofuran. Lower temperatures are also effective, however, the cyclodehydration is slower. To be effective alone, the temperature must be at least about 50° C. Similarly, higher temperatures are also effective; however, they are considered wasteful and can cause unwanted isomerizations. In any event, temperatures in excess of about 300° C. should be avoided because such temperatures will severely degrade the products. A combination of acidic environment and elevated temperature also can be used.

A small amount of menthofuran can be formed during the oxidation step of the instant process if said step is carried out in a slightly acidic environment or at a slightly elevated temperature. In any event, the reaction sequence is the same. In such case the oxidation reaction conditions are merely effective to also partially cyclodehydrate the isopulegone epoxide formed to menthofuran.

The menthofuran containing products produced by the foregoing process can optionally be further purified and concentrated. Any of the procedures known in the art for purification of organic compounds can be used. An example of such processes is fractional distillation. For example, a spinning band column can be used to distill the product. Such distillation can readily produce fractions or cuts containing at least about 90% menthofuran and, in some cases, as high as 99+%, with little or no loss.

The following examples show ways we have operated our process and obtained menthofuran. The examples should not be construed as limiting the invention. All temperatures are given in degrees Centigrade and all percentages are weight percentages unless otherwise specified.

EXAMPLE 1

Into a 3-liter, 3-neck flask, fitted with a thermometer, addition funnel, and a stirrer, were placed 308 g. (2 moles) of isopulegol, 400 g. (3.8 moles) of sodium carbonate, and 900 ml. methylene chloride. The reaction mixture was cooled to about 0° C. and 320 ml. (about 2.5 moles) of 40% peracetic acid containing 12 g. sodium acetate was added. The addition was controlled so that a reaction temperature of about 25° C. was maintained. The addition took about 30 minutes. The flask was held at 25° to 30° C. for 3 hours. The reaction mixture was allowed to stir overnight. In order to work up, water was added to dissolve the salts. The organic portion was then washed with water, cold 5% sodium hydroxide, sodium bisulfite solution, and water successively. Solvent was removed in a rotary evaporator at 35° to 40° C. About 418 g. of product was obtained, containing about 63% isopulegol epoxide (3-hydroxy-p-menthan-8,9-oxide) and about 15% methylene chloride solvent. This represents a yield of isopulegol epoxide of 77% based on the charged isopulegol.

Into a 500 ml. round bottomed, 3-necked flask fitted with a thermometer, stirrer, and an addition funnel were charged 40 g. (0.148 moles) of the above product and 60 ml. of pyridine. The reaction mixture was cooled with stirring to about 5° C. Separately, 100 ml. of methylene chloride was placed in a 250 ml. round bottomed flask and stirred at −40° C., then 12.6 g. (0.177 moles) of chlorine gas was dissolved into the methylene chloride. This represents a molar ratio of isopulegol epoxide to chlorine of 1.0 to 1.2.

The chlorine solution was taken into the addition funnel and added to the above 500 ml. flask at a temperature of 10° C. during a period of 25 minutes. This reaction mixture was brought to a temperature of 25° to 30° C. and maintained for 20 minutes. Vapor Phase Chromatographic (VPC) analysis revealed that all of the epoxide was consumed. The reaction mixture was quenched with water and worked up to give 43.7 g. of product containing 40.3% pyridine, 5.4% menthofuran, and 41.3% cis- and trans-isopulegone epoxide.

The product was stirred with two 50 ml. portions of 9% hydrochloric acid at room temperature. A small amount of pentane was added to break the emulsion. The organic portion was washed with water and sodium bicarbonate solution to remove any acid present. After the removal of pentane, the oil was stripped in the presence of potassium stearate to give 18.5 g. of a distillate containing 83.8% menthofuran and 6.5 g. of residue.

The yield of menthofuran based on isopulegol epoxide was 69.2%.

EXAMPLE 2

In the procedure of Example 1, 0.147 moles of isopulegol epoxide and 0.20 moles of chlorine gas were reacted. This is a ratio of isopulegol epoxide to chlorine of 1.0 to 1.4 on a molar basis. The yield of menthofuran based on isopulegol epoxide was 61.7%.

EXAMPLE 3

In the procedure of Example 1, 0.59 moles of isopulegol epoxide and 1.1 moles of chlorine gas were used in the reaction. This is a molar ratio of isopulegol epoxide to chlorine gas of 1.0 to 1.86. When the reaction mixture was quenched with water and worked up, Vapor Phase Chromatography (VPC) indicated it contained 10.4% menthofuran. When this product was treated twice with a 50-ml. portion of 3% hydrochloric acid solution, the percentage of menthofuran increased to 21.2%. When this product was similarly treated with a 9% hydrochloric acid solution, the percentage of menthofuran increased to 65.7% and there was no longer any trace of isopulegone epoxide in the product mixture. The yield of menthofuran based on isopulegol epoxide was 48.2%.

EXAMPLE 4

In the procedure of Example 1, 25 g. of crude isopulegone epoxide reaction mixture containing 11.6% pyridine, 18.6% menthofuran, and 51.1% cis- and trans-isopulegone epoxide was thermally cyclized in a spinning band column. The column operated at reflux ratio of 5:1. The pot temperature was 110° to 115° C. and the pressure was held at 1 mm. of mercury. The distilled cuts contained about 12 g. of menthofuran of about 90 to 98% purity. There was 24% residue obtained in this distillation. The yield of pure menthofuran was 59% based on isopulegone epoxide in the crude isopulegone epoxide reaction mixture used as starting material (not including any menthofuran present in the starting material).

EXAMPLE 5

To a magnetically stirred mixture containing 30.8 g. (0.2 mol) isopulegol, 10.2 g. (0.2 mol) acetonitrile, and 3.4 g. potassium bicarbonate in 100 ml. methanol was added dropwise 13.6 ml. (0.2 mol) of a 50% hydrogen peroxide solution. After addition, the reaction mixture was left at room temperature for 4 days and then evaporated. The residue was washed with water, dried and distilled to give 32.0 g. of isopulegol epoxides (3-hydroxy-p-menthan-8,9-oxide), a yield of 94%.

EXAMPLE 6

A solution of 33 mmoles oxalyl chloride in 25 ml. of methylene chloride was stirred and brought to a temperature of −60° C. under nitrogen over a 5-minute period and then 64 mmoles of dimethyl sulfoxide in 25 ml. methylene chloride was added through an addition funnel. To the resulting solution 29 mmoles of isopulegol epoxide in 25 ml. methylene chloride was added over a 5-minute period. The reaction mixture was stirred at −60° C. for 15 minutes followed by a dropwise addition of 100 mmoles of triethylamine. The reaction was allowed to warm to room temperature and then 100 ml. of water was added. The organic layer produced was analyzed by Vapor Phase Chromatography (VPC) and contained 65.7% isopulegone epoxides and 2.2% starting material.

EXAMPLE 7

A solution of 29 mmoles of isopulegol epoxide and 36 mmoles of pyridinium dichromate in 35 ml. dimethylformamide was stirred at 0° C. for 4 hours. Then 100 ml. water and 50 ml. pentane were added. The pentane extract was separated and dried. Vapor Phase Chromatographic (VPC) analysis showed it contained 39.7% isopulegone epoxide, 31.3% starting material, and 7.0% menthofuran.

What is claimed is:

1. A process for synthesizing menthofuran comprising:
   epoxidizing isopulegol under epoxidizing conditions to form isopulegol epoxide,
   oxidizing the hydroxyl of said isopulegol epoxide under oxidizing conditions to form isopulegone epoxide, and
   cyclodehydrating said isopulegone epoxide under cyclodehydrating conditions to form menthofuran.
2. The process of claim 1 wherein said isopulegol is epoxidized with a peracid.
3. The process of claim 1 wherein said isopulegol is epoxidized with an alkyl, aryl, or aralkyl nitrile containing 2 to 12 carbon atoms with hydrogen peroxide.
4. The process of claim 3 wherein said nitrile is acetonitrile.
5. The process of claim 1 wherein said hydroxyl of isopulegol epoxide is oxidized using chlorine and pyridine.
6. The process of claim 1 wherein said cyclodehydration of isopulegone epoxide takes place in an acidic environment.
7. The process of claim 1 wherein said cyclodehydration of isopulegone epoxide takes place at a temperature of between 50° C. and 300° C.
8. The process of claim 1 wherein the menthofuran-containing product is further concentrated.
9. The process of claim 1 wherein the menthofuran-containing product is distilled and recovered to yield a product containing at least about 90% menthofuran.
10. In the process of claim 1 wherein the menthofuran formed is optically active.
11. In the process of claim 1 wherein the menthofuran formed is optically inactive.
12. A method for enhancing the yield of menthofuran from a process wherein isopulegone epoxide is an intermediate, which comprises:
    the step of oxidizing the hydroxyl of isopulegol epoxide under oxidizing conditions to form isopulegone epoxide.
13. The method of claim 12 further comprising:
    cyclodehydrating said isopulegone epoxide to form menthofuran.

* * * * *